US005523215A

United States Patent [19]

Cousens et al.

[11] Patent Number: 5,523,215
[45] Date of Patent: Jun. 4, 1996

[54] ENHANCED PURIFICATION AND EXPRESSION OF INSOLUBLE RECOMBINANT PROTEINS

[75] Inventors: Lawrence S. Cousens, Oakland; Patricia Tekamp-Olson, San Anselmo, both of Calif.

[73] Assignee: Chiron Corporation, Emeryville, Calif.

[21] Appl. No.: 869,613

[22] Filed: Apr. 16, 1992

Related U.S. Application Data

[63] Continuation-in-part of Ser. No. 680,046, Mar. 29, 1991, Pat. No. 5,342,921, which is a continuation of Ser. No. 169,833, Mar. 17, 1988, abandoned, which is a division of Ser. No. 845,737, Mar. 28, 1996, Pat. No. 4,751,180, which is a continuation-in-part of Ser. No. 717,209, Mar. 28, 1985, abandoned.

[51] Int. Cl.⁶ .............................. C12N 1/15; C12N 1/21; C12N 15/09; C07K 1/00
[52] U.S. Cl. .................. 435/69.1; 435/252.33; 435/254.21; 530/418; 530/420
[58] Field of Search ............................. 530/412, 414, 530/418, 420, 427; 435/69.1, 803, 70.1, 71.1, 252.33, 254.21, 172.3

[56] References Cited

U.S. PATENT DOCUMENTS

| 4,656,131 | 4/1987 | Kitano | 435/69.51 |
| 4,748,234 | 5/1988 | Dovin | 530/412 |
| 5,342,921 | 8/1994 | Cousens | 530/324 |

OTHER PUBLICATIONS

Mitraki et al., Protein Folding Intermediates and Inclusion Body Formation (1989) Biotechnology 7: 690–697.
Georgiou, G., AIChE Journal, 34(8):1233–1248 (1988).

*Primary Examiner*—Dian C. Jacobson
*Attorney, Agent, or Firm*—Ling-Fong Chung; Grant Green; Robert P. Blackburn

[57] ABSTRACT

A method for isolating a desired protein which comprises: providing a host cell expressing the desired protein as an insoluble aggregate; culturing the host cell with an effective mount of $Cu^{++}$; disrupting the host cell producing a lysate; incubating the insoluble fraction non-disulfide-bond reducing or non-copper competing chaotropic conditions to solubilize contaminants; separating the insoluble from the soluble fraction; and exposing the insoluble fraction to disulfide-bond reducing or copper competing chaotropic conditions to solubilize the desired protein.

19 Claims, No Drawings

ENHANCED PURIFICATION AND EXPRESSION OF INSOLUBLE RECOMBINANT PROTEINS

CROSS-REFERENCE TO RELATED APPLICATIONS

This application is a continuation-in-part of U.S. patent application Ser. No. 07/680,046 filed Mar. 29, 1991, now U.S. Pat. No. 5,342,921, which is a continuation of U.S. patent application Ser. No. 07/169,833 fried Mar. 17, 1988, now abandoned, which is a divisional of U.S. patent application Ser. No. 06/845,737 fried Mar. 28, 1986 now U.S. Pat. No. 4,751,180, which is a continuation-in-part of U.S. patent application Ser. No. 717,209 filed Mar. 28, 1985, now abandoned. All of the referenced applications are incorporated herein by reference in full.

DESCRIPTION

1. Technical Field

This invention relates to increasing intercellular expression of heterologous proteins in host cells and an improved method of purifying intracellularly expressed proteins from host cells.

2. Background of the Invention

Using recombinant DNA technology, protein products can be produced in large quantities. One of the preferred methods of accomplishing this is to express the protein intracellularly. This may result in production of large quantities of insoluble, intracellular protein found in inclusion bodies, for example in the case of expression of fusion proteins. Although such proteins may not be native in structure, they can sometimes be renatured or used "as is," e.g. for immunodiagnostics. The major advantage of this approach is that it can yield very high levels of product.

Recombinant proteins produced as insoluble products in inclusion bodies have solubility properties that may interfere with their purification. These proteins generally require use of a denaturant, chaotrope or detergent for solubilization. In some cases, these treatments prevent the use of certain chromatographic procedures for purification, such as ion exchange. In addition, these treatments can solubilize non-proteinaceous contaminants that interfere with downstream processing, such as high molecular weight carbohydrates that may increase the viscosity of the solution.

3. Disclosure of the Invention

Accordingly, it is an object of the invention to provide a separation method that purifies the desired insoluble protein based only on its solubility characteristics. The method comprises:

culturing a host cell in an effective amount of $Cu^{++}$;

disrupting the host cell to produce a cell lysate;

exposing the lysate to non-disulfide bond reducing or non-copper competing chaotropic conditions;

separating the soluble contaminants from the insoluble pellet containing the desired protein; and incubating the pellet under disulfide bond reducing or copper competing chaotropic conditions.

Another object of the invention to provide a method for increasing insoluble protein expression. The process comprises:

providing host cell capable of expressing the desired protein;

also providing an expression vector that does not contain any DNA encoding a functional metallothionein or a promoter regulated by $Cu^{++}$ concentration; and culturing the host cell in the presence of an amount of $Cu^{++}$ effective to increase expression.

A further object of the invention is an inclusion body comprising a protein aggregate obtained by the process comprising:

culturing the host cell that expresses the desired protein in an effective amount of $Cu^{++}$;

disrupting the host cell to produce a cell lysate; and separating said soluble fraction of the lysate from said insoluble fraction.

MODES OF CARRYING OUT THE INVENTION

A. Definitions

An "expression vector" comprises a coding sequence operably linked to any necessary control sequences, such as a promoter, terminator, and optionally a selectable marker. These control sequences are "operable" in a host cell if they enable the host cell to express the coding sequence. An expression vector "free of functional metallothionein DNA" will not contain any DNA encoding a copper binding protein operable in the host.

A "promoter" is a DNA sequence that initiates and regulates the expression of a coding sequence when the promoter is operably linked to the coding sequence. A promoter is "not regulated by $Cu^{++}$ concentration" if the promoter is not triggered or modulated by the presence or concentration of $Cu^{++}$ ions. For example, the bacterial lac promoter is triggered by the presence of lactose and is not regulated by $Cu^{++}$ concentration. Metallothionein promoters are triggered by the presence of $Cu^{++}$ ions.

A "coding sequence" is a nucleic acid sequence that encodes a protein or peptide. A "non-copper containing protein" does not specifically bind copper (e.g. insulin). An example of a copper containing protein is superoxide dismutase, a protein that has a specific copper binding site.

"Contaminants" are any organic or inorganic matter (aside from solvents, and the like) that are not the desired protein.

"Non-disulfide bond reducing chaotropic conditions" are conditions that denature proteins but do not break disulfide bonds between cysteine residues. During this step, the desired protein remains insoluble. Such conditions are capable of solubilizing the contaminant proteins by either altering, for example, the state of hydration, the solvent environment, or the solvent-surface interaction. Examples of these conditions are effective amounts of urea, tetramethylurea, guanidine hydrochloride, sodium thiocyanate, and detergents, such as SDS. An "effective amount of a non-disulfide reducing chaotropic agent" is the amount necessary to solubilize a substantial portion of the contaminants from the insoluble desired protein. These agents can be used alone or in combination. Depending on the agent or the combination of agents, the effective concentration will vary. Typically, the concentration of a non-disulfide reducing chaotropic agent (e.g. SDS) will be no greater than 10%; more typically, the concentration will be no greater than 7.5%; preferably, the concentration will be no greater than 5%. Additionally, the concentration usually will not be less than 0.1%, more usually the concentration will not be less than 0.25%, preferably not less than 0.5%. The optimal concentration will vary from protein to protein and host cell to host cell but may be determined empirically by routine experimentation.

"Disulfide-bond reducing chaotropic conditions" are conditions that denature proteins and break disulfide bonds. In addition to the above mechanisms, such conditions alter the solubility of proteins by breaking disulfide bonds that constrain the molecule. Examples of these conditions are effective amounts of any of the above non-disulfide bond reducing chaotropic agents in combination with a disulfide bond reducing agent such as: dithiothreitol, β-mercaptoethanol, dithioerythritol, thioglycerol, tris(2-carboxyethyl)phosphine (TCEP) (Burns et al. *J. Org. Chem.* 56:2648–2650 (1991)), and N,N'-dimethyl-N,N'-bis(mercaptoacetyl)hydrazine (Singh et al. *J. Org. Chem.* 56: 2332–2337 (1991)). Depending on the combination of agents the effective concentrations will vary. Typically, the concentration of a non-disulfide reducing chaotropic agent (e.g. SDS) will be no greater than 10%; more typically, the concentration will be no greater than 7.5%; preferably, the concentration will be no greater than 5%. Additionally, the concentration usually will not be less than 0.1%, more usually the concentration will not be less than 0.25%, preferably not be less than 0.5%. An "effective amount of a disulfide-bond reducing agent" is an mount that breaks enough disulfide bonds to solubilize a substantial portion of the desired protein. Typically, the concentration of a disulfide reducing bond agent (e.g. DTT) will be no greater than 100 mM; more typically, the concentration will be no greater than 75 mM, preferably no greater than 50 mM. Additionally, the concentration usually will not be less than 1 mM; more usually the concentration will not be less than 5 mM, preferably not be less than 10 mM. Optimal concentrations will vary from protein to protein and host cell to host cell but may be determined by routine experimentation.

"Non-copper competing chaotropic conditions" will not compete with the desired protein for copper by, for example, binding or reacting with the copper. Thus, the copper is not dissociated from the desired protein, which remains insoluble. Such conditions can solubilize contaminants by either altering, for example, the state of hydration, the solvent environment, or the solvent-surface interaction. Examples of these conditions are effective amounts of urea, tetramethylurea, guanidine hydrochloride, and detergents, such as SDS. An "effective amount of a non-copper competing chaotropic agent" is the amount necessary to solubilize a substantial portion of contaminants while leaving the desired protein insoluble. These agents can be used alone or in combination. Depending on the agent or combination of agents, the effective concentration will vary. Typically, the concentration of a non-copper competing chaotropic agent (e.g. SDS) will be no greater than 10%; more typically, the concentration will be no greater than 7.5%; preferably, the concentration will be no greater than 5%. Additionally, the concentration usually will not less than 0.1%, more usually the concentration will not be less than 0.25%, preferably not be less than 0.5%. The optimal concentration will vary from protein to protein and host cell to host cell, but may be determined empirically by routine experimentation.

"Copper competing chaotropic conditions" compete or displace copper from the desired protein by binding or reacting with the metal ion. Under these conditions, the copper ion is dissociated from the desired protein, which is rendered soluble. In addition to non-copper competing chaotropic agent(s), these conditions can also comprise a copper competing agent. An "effective mount of copper competing agent" will be an amount that solubilizes a substantial portion of the desired protein. An example of copper competing agents is DTT. Depending on the combination of agents the effective concentrations will vary. Typically, the concentration of a non-copper competing chaotropic agent (e.g. SDS) will be no greater than 10%; more typically, the concentration will be no greater than 7.5%; preferably, the concentration will be no greater than 5%. The concentration usually will not be less than 0.1%, more usually the concentration will not be less than 0.25%, preferably not less than 0.5%. Also, the concentration of copper competing agent (e.g. DTT) will usually be no greater than 100 mM; more typically the concentration will be no greater than 75 mM, preferably no greater than 50 mM. The concentration usually will not be less than 1 mM; more usually the concentration will not be less than 5 mM, preferably not less than 10 mM. Optimal concentrations will vary from protein to protein and host cell to host cell but may be determined by routine experimentation.

"Medium with enhanced aeration" is a solution of nutrients for the host cell enhanced with dissolved oxygen. The oxygen can be added to the medium, for example, in the form of $O_2$ or a mixture of gases, such as air. The amount of gas dissolved can be controlled by standard means, e.g., by adjusting the amount of gas bubbled into the medium, adjusting the stirring or shaking rate, adjusting the temperature of the medium, regulating the surface area of the volume of medium and the like. Agitating the medium can also increase the percentage of dissolved oxygen. In general, "enhanced aeration" means that the medium will contain a higher concentration of dissolved $O_2$ than a similar medium which is not agitated or otherwise aerated. Usually, the concentration of dissolved oxygen will be between 30% and 100% partial pressure, typically no greater than 60% partial pressure. The optimal concentration will vary from protein to protein and from host cell to host cell but may be determined by routine experimentation.

An "effective amount of $Cu^{++}$" is an amount sufficient to decrease the solubility of the desired protein, i.e. the protein will be resistant to solubilization under non-disulfide bond reducing or non-copper competing chaotropic conditions that solubilize most contaminants. The exact amount will vary depending on the protein and host cell, but can be determined empirically by examining the solubility properties of the expressed protein, e.g. on a SDS-PAGE gel. $Cu^{++}$ can be added to the medium in the form of copper sulfate or copper chloride, for example. Typically, the concentration of $Cu^{++}$ will be no greater than 100 mM; more typically, the concentration will be no greater than 20 mM, preferably no greater than 5 mM. Additionally, the concentration usually will not be less than 10 μM; more usually the concentration will not be less than 100 μM, preferably not less than 500 μM. The optimal concentration will vary depending on the desired protein, host cell, and medium but may be determined by routine experimentation.

An "amount of $Cu^{++}$ effective to increase expression" increases the amount of desired protein produced. The production of desired protein has increased if more protein is expressed when the host cells are cultured with than without $Cu^{++}$. Typically, the concentration of $Cu^{++}$ will be no greater than 100 mM; more typically, the concentration will be no greater than 20 mM, preferably no greater than 5 mM. Additionally, the concentration usually will not be less than 10 μM; more usually, the concentration will not be less than 100 μM; preferably not less than 500 μM. The optimal concentration will vary depending on the desired protein, host cell, and medium but may determined by routine experimentation.

The term "HIV env protein" refers to an envelope protein from a human immunodeficiency virus, such as gp120 and gp41 found in HIV-1 and HIV-2. "HIV env protein" includes both full-length proteins and antigenic fragments thereof (capable of immunoreactivity with anti-HIV antibodies). "Env2-3" is also an HIV env protein. The sequence is described by Luciw et al. Nature 312:760–763 (1984). Env2-3 may include a fragment or epitope of the envelope protein. Preferably, it consists of amino acids 26 to 510 of gp120.

"IL-2" is either a portion or the complete intefleukin-2 protein. The amino acid sequence is described in U.S. Pat. No. 4,518,584. Generally, IL-2 will include a substantial portion of the complete protein.

"IFN-β" refers to an interferon-β, such as IFN-$β_1$, IFN-$β_2$, and the like, or a fragment thereof. See U.S. Pat. No. 4,518,584 for the amino acid sequence. Typically, the terms refers to a substantial portion of the protein.

"M-CSF" refers to macrophage colony stimulating factor or a fragment thereof. Its amino acid sequence is described in U.S. Pat. No. 4,929,700. Preferably, M-CSF includes amino acids 4 to 221 of the long clone with a mutation at position 59 from tyrosine to aspartate.

Fusion proteins expressed using the method of the invention include the following proteins: human Cu/Zn superoxide dismutase (SOD), human proinsulin, the putative Hepatitis C virus core (CORE), envelope (E1), non-structural 3, 4, and 5 (NS3, NS4, & NS5)proteins.

The sequences of the above proteins are known in the art. The sequence of SOD is described in PCT WO85/01503. The human proinsulin sequence is described in Bell et al. Nature 282:525–527 (1979). The entire amino acid sequence of HCV1 is described in EPO 388 232. The fusion proteins below can include fragments of the proteins listed above, but generally will contain a substantial portion of the complete polypeptide sequence. HCV1 is expressed naturally as a polyprotein. Any number of epitopes from the polyprotein can be useful as an immunodiagnostic. Epitopes from the following putative proteins particularly can be utilized: amino acids 1 to 192 (CORE); amino acids 191 to 384 (E1); amino acids 1000 to 1500 (NS3); amino acids 1500 to 1960 (NS4); and amino acids 1960 to 3011 (NS5).

"SOD/E1" refers to a fusion protein containing human Cu/Zn SOD sequence fused to a portion of the E1 region of HCV, preferably a fusion of the entire SOD amino acid sequence and amino acids 199 to 329 of HCV1 from amino to carboxyl terminus of the fusion.

"SOD/PI" preferably is a protein that includes from the amino to carboxyl terminus the entire SOD protein linked to entire proinsulin gene by a linker with the amino acid sequence NSGPTPPSPGSPKR.

"SOD/PI/E1" is a fusion protein that includes preferably the entire SOD gene, the entire proinsulin protein, a Lys-Arg-Ser-Asn-Ser-Thr linker, and amino acids 199 to 329 of HCV1, amino to carboxyl terminus.

"C25" refers to a fusion of the entire SOD protein, which is linked at its carboxyl end to a portion of the NS3 region of HCV, preferably amino acids 1192 to 1931 of HCV1, which is linked to a portion of the core region of HCV, preferably amino acids 1 to 120 of HCV1.

"SOD/NS5" refers to a protein that contains (amino to carboxyl) the entire SOD protein linked to a portion of the NS5 region of HCV, preferably amino acids 2054 to 2995 of HCV1.

B. General Method

Suitable proteins for the purification and expression methods will react with $Cu^{++}$. The desired protein may react with the $Cu^{++}$ by binding non-specifically with the metal. Alternatively, the copper ion may bond with cysteine, methionine or histidine residues to reduce solubility. Also, $Cu^{++}$ may catalyze disulfide formation.

Thus, the instant invention may be more effective if additional cysteine, methionine or histidine residues, which may bind or react with $Cu^{++}$, are incorporated into the desired protein. For example, the gene encoding the protein may be altered by in vitro mutagenesis to change residues to cysteine, for example. This is done using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having the mutated form as a single strand; 50% will have the original sequence. The resulting plaques are hybridized with kinased synthetic primer under allele-specific conditions. In general, one may vary the temperature, ionic strength, and concentration of chaotropic agent(s) in the hybridization solution to obtain conditions under which substantially no probes will hybridize in the absence of an "exact match." For hybridization of probes to bound DNA, the empirical formula for calculating optimum temperature under standard conditions (0.9M NACl) is $$T(° C.)=4(N_G+N_C)+2(N_A+N_T)-5° C.,$$

where $N_G$, $N_C$, $N_A$, and $N_T$ are the numbers of G, C, A, and T bases in the probe (J. Meinkoth et al, *Anal Biochem* (1984) 138:267–84). Plaques which hybridize with the probe are then picked, cultured, and the DNA recovered.

Alternatively, a nucleic acid oligomer encoding a cysteine residue rich peptide, for instance, can be added to the gene of the desired protein. The oligomer can be added either to the 5' or 3' end of the desired protein gene. For convenience, the cysteine rich peptide may contain a cleavage site so that the peptide may be cleaved from the desired protein sequence. Examples of such sites are dibasic residues cleavable by KEX2 protease and Glu-Ala residues clearable by dipeptidylaminopeptidase A. These oligomers encoding the peptide may be produced by synthetic procedures, such as the triester method of Matteucci et at. (*J. Am. Chem. Soc.* (1981) 103:3185), or according to Urdea et al. *Proc. Natl. Acad. Sci. USA* 80: 7461 (1983), or using commercially available automated oligonucleotide synthesizers. After the nucleic acid oligomer is made, it can be ligated to the desired gene according to the procedures in Sambrook et al., "Molecular Cloning: A Laboratory Manual" (New York, Cold Spring Harbor Laboratory, 1989).

The desired protein gene sequence may be obtained either through publically available databanks, e.g. Gertbank, or nucleic acid gene libraries. These sequences can be synthesized or cloned. Techniques for producing and probing nucleic acid sequence libraries are described, for example, in Sambrook et al., "Molecular Cloning: A Laboratory Manual" (New York, Cold Spring Harbor Laboratory, 1989). Synthetic oligonucleotides can also be used to generate the necessary gene.

Insoluble aggregates of the desired protein can be formed from homologous proteins, as well as heterologous proteins. For example, altered conditions within the normal host can result in inclusion body formation of wild-type *E. coli* proteins. See Botterman et at., *Gene* 37:229–239 (1985) and Schomaker et at. *E.M.B.O.* 4:775–780 (1985).

Usually, the desired protein will be heterologous to the host cell and expressed via an expression vector. The vector will comprise at least a promoter and terminator operably linked to the gene encoding the desired protein (and any modifications). These expression vector elements must be operable in the chosen host cell. Typically, the expression vector will also contain a selectable marker and an origin of replication.

A promoter is a DNA sequence usually upstream or 5' of the gene to be expressed. This DNA sequence will initiate and regulate expression of the coding sequence. To initiate expression, promoter sequences are capable of binding RNA polymerase and initiating the downstream (3") transcription of a coding sequence (e.g. structural gene) into mRNA. A promoter may also have DNA sequences that can regulate the rate of expression by enhancing or specifically inducing or repressing transcription. These sequences can overlap promoter sequences that initiate expression. Most host cell systems possess regulatory promoter sequences. For example, a repressor protein in *E. coli* can bind the Inc operator and thereby inhibit transcription of the 5' gene. Mother example is the yeast alcohol dehydrogenase promoter, which has an upstream activator sequence (UAS) that modulates expression in the absence of a readily available source of glucose. Additionally, some vital enhancers not only amplify but also regulate expression in mammalian cells. These enhancers become active only in the presence of an inducer, such as a hormone or enzyme substrate (Sassone-Corsi and Borelli (1986) *Trends Genet.* 2:215; Maniatis et al. (1987) Science 236:1237).

Functional non-natural promoters may also be used, for example, synthetic promoters based on a consensus sequence of different promoters. Also, one may use promoters, which contain a regulatory region linked with a heterologous expression initiation region. Examples of hybrid promoters are the *E. coli* lac operator linked to the *E. coli* tac transcription activation region; the yeast alcohol dehydrogenase (ADH) regulatory sequence linked to the yeast glyceraldehyde-3-phosphate-dehydrogenase (GAP) transcription activation region (U.S. Pat. Nos. 4,876,197 and 4,880,734); and the cytomegalovirus (CMV) enhancer linked to the SV40 (simian virus) promoter.

Typically, terminators are regulatory sequences located 3' of the stop codon of the coding sequences, such as polyadenylation and transcription termination sequences. Usually, the terminator of native host cell proteins are operable when attached 3' of the desired protein's coding sequences. Examples are the Saccharomyces cerevisiae alpha-factor terminator and the baculovirus terminator. Further, viral terminators are also operable in certain host cells; for instance, the SV40 terminator is functional in Chinese Hamster Ovary cells.

For convenience, selectable markers, an origin of replication, and homologous host cells sequences may also optionally be included in an expression vector. A selectable marker can be used to screen for host cells that potentially contain the expression vector. Such markers may render the host cell immune to drugs such as ampicillin, chloramphenicol, erythromycin, neomycin, and tetracycline. Also, markers may be biosynthetic genes, such as those in the histidine, tryptophan, and leucine pathways. Thus, when leucine is absent from the media, for example, only the cells with a biosynthetic gene in the leucine pathway will survive.

An origin of replication may be needed for the expression vector to replicate in the host cell. With certain origins of replication, an expression vector can be reproduced at a high copy number in the presence of the appropriate proteins within the cell. Examples of origins are the 2μ and autonomously replicating sequences, which are effective in yeast; the vital T-antigen, effective in COS-7 cells.

Expression vectors may integrate into the host cell genome or remain autonomous within the cell. To integrate, sequences homologous to sequences within the host cell genome must be provided. The homologous sequences do not always need to be linked to the expression vector to be effective. For example, expression vectors can integrate into the Chinese Hamster Ovary cell (CHO) genome via an unattached dihydrofolate reductase gene. In yeast, it is more advantageous if the homologous sequences flank the expression vector. Particularly useful homologous yeast genome sequences are disclosed in PCT WO90/01800. In insect host cells, homologous baculovirus sequences are used to recombine with the virus that infects the cell. See Smith et al., *Mol. Cell. Biol.* (1983) 3:2156; and Luckow and Summers *Virology* 17:31 (1989).

The choice of promoter, terminator, and other optional elements of an expression vector depend on the host cell chosen. The invention is not dependent on the host cell selected. Convenience and the desired protein will dictate the optimal host cell. A variety of hosts for expression are known in the art and available from the American Type Culture Collection (ATCC). Bacterial hosts suitable for expressing a desired protein include, with limitation: Campylobacter, Bacillus, Escherichia, Lactobacillus, Pseudomonas, Staphylococcus, and Streptococcus. Yeast hosts from the following genera may be utilized: Candida, Hansenula, Kluyveromyces, Pichia, Saccharomyces, Schizosaccharomyces, and Yarrowia. Immortalized mammalian host cells include but are not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. A number of insect cell hosts are also available for expression of heterologous proteins: *Aedes aegypti, Autographa californica, Bombyx mori, Drosophila melanogaster,* and *Spodoptera frugiperder* (PCT WO 89/046699; Carbonell et at., (1985) *J. Virol.* 56:153; Wright (1986) *Nature* 321:718; Smith et at., (1983) *Mol. Cell. Biol.* 3:2156; and see generally, Fraser, et al. (1989) *In Vitro Cell. Dev. Biol.* 25:225).

The transformation procedure to introduce the expression vector depends upon the host to be transformed. Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation or vital infection. Transformation procedures usually vary with the bacterial species to be transformed. See e.g., (Masson et al. (1989) *FEMS Microbiol. Lett.* 60:273; Palva et al. (1982) *Proc. Natl. Acad. Sci. USA* 79:5582; EPO Publ. Nos. 036 259 and 063 953; PCT WO 84/04541, Bacillus), (Miller et al. (1988) *Proc. Natl. Acad. Sci.* 85:856; Wang et al. (1990) *J. Bacteriol.* 172:949, Campylobacter), (Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318; Escherichia), (Chassy et al. (1987) *FEMS Microbiol. Lett.* 44:173

Lactobacillus); (Fiedler et al. (1988) Anal. Biochem 170: 38, Pseudomonas); (Augustin et al. (1990) *FEMS Microbiol. Lett.* 66:203, Staphylococcus), (Barany et al. (1980) *J. Bacteriol.* 144:698; Harlander (1987) "Transformation of Streptococcus lactis by electroporation, in: *Streptococcal Genetics* (ed. J. Ferretti and R. Curriss III); Perry et al. (1981) *Infec. Immun.* 32:1295; Powell et al. (1988) Appl. Eviron. Microbiol. 54:655; Somkuti et al. (1987) *Proc. 4th Evr. Cong. Biotechnology* 1:412, Streptococcus).

Transformation methods for yeast hosts are well-known in the art, and typically include either the transformation of spheroplasts or of intact yeast cells treated with alkali cations. Transformation procedures usually vary with the yeast species to be transformed. See e.g., (Kurtz et al. (1986) *Mol. Cell. Biol.* 6:142; Kunze et al. (1985) *J. Basic Microbiol.* 25:141; Candida); (Gleeson et al. (1986) *J. Gen. Microbiol.* 132:3459; Roggenkamp et al. (1986) *Mol. Gen. Genet.* 202:302; Hansenula); (Das et al. (1984) *J. Bacteriol.* 158:1165; De Louvencourt et al. (1983) *J. Bacteriol.* 15.4:1165; Van den Berg et al. (1990) *Bio/Technology* 8:135; Kluyveromyces); (Cregg et al. (1985) *Mol. Cell. Biol.* 5:3376; Kunze et al. (1985) *J. Basic Microbiol.* 25:141; U.S. Pat. Nos. 4,837,148 and 4,929,555; Pichia); (Hinnen et al. (1978) *Proc. Natl. Acad. Sci. USA* 75;1929; Ito et al. (1983) *J. Bacteriol.* 153:163 Saccharomyces); (Beach and Nurse (1981) *Nature* 300:706; Schizosaccharomyces); (Davidow et al. (1985) *Curr. Genet.* 10:39; Gaillardin et al. (1985) *Curr. Genet.* 10:49; Yarrowia).

Methods for introducing heterologous polynucleotides into mammalian cells are known in the art and include viral infection, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Methods for introducing heterologous DNA into the baculovirus virus and consequently an insect host cell are known in the art. (See Smith et al., *Mol. Cell. Biol.* (1983) 3:2156; and Luckow and Summers Virology 17:31 (1989)). For example, the insertion can be into a gene such as the polyhedrin gene, by homologous double crossover recombination; insertion can also be into a restriction enzyme site engineered into the desired baculovims gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. The polyhedrin protein produced by the native virus at very high levels in the nuclei of infected cells at late times after viral infection. Accumulated polyhedrin protein forms occlusion bodies that also contain embedded particles. These occlusion bodies, up to 15 μm in size, are highly refractile, giving them a bright shiny appearance that is readily visualized under the right microscope. Cells infected with recombinant viruses lack occlusion bodies. To distinguish recombinant virus from wild-type virus, the transfection supernatant is plaqued onto a monolayer of insect cells by standard techniques. Typically, the plaques are screened under the right microscope for the presence (indicative of wild-type virus) or absence (indicative of recombinant virus) of occlusion bodies. ("Current Protocols in Microbiology" Vol. 2 (Ausubel et at. eds) at 16.8 (Supp. 10, 1990))

The medium to culture host cells will vary depending on the specific cell type chosen. Generally, the medium will contain all the nutrients needed to propagate the cells, e.g. amino acids, sugars, lipids, salts, vitamins, etc. Additional ingredients such as antibiotics, to limit growth of unwanted cells, or compounds like methotrexate, to enhance or induce expression, may also be included. Other factors, such as temperature, aeration, and pH, may need to be controlled and optimized. To aerate the medium, the gas mixture can be bubbled directly into the medium or supplemented to the exposed surface of the medium. Agitating the medium will help dissolve the gas into the media in both cases.

$Cu^{++}$ ions can be added to the media in the form of copper salts, such as copper sulfate or copper chloride. The copper ions can be present in the media throughout incubation of the host cells, but can be added immediately prior to protein expression. For instance, in *E. coli* expression, copper may be added when protein expression is induced with IPTG. Mother important consideration is that the media components do not chelate all of the copper ions. For example, excess citrate, which binds copper, may reduce the effective $Cu^{++}$ concentration.

After culturing the cells, the medium is generally separated from the cells, usually by centrifugation, before the cells are disrupted. Next, sonicating or homogenizing the cell pellet, for example, is effective to break the cells and produce a cell lysate. Alternatively, certain host cells may be disrupted by enzymatic digestion of the cell wall or membrane. The digestion can be followed by osmotic shock, sonication, or detergent, if necessary. Lysozyme is commonly used for these enzymatic process. Autolysis and toluene are also effective for disrupting cells. Mammalian cells are easily disrupted by detergents or shearing.

Preferably, the soluble fraction is separated from the cell lysate. Typically, the insoluble material is pelleted by centrifugation, and the soluble fraction is removed. For large scale purification operations, filtering the cell lysate may be more economical. Such filtering methods include ultrafiltration and diafiltration.

The insoluble fraction is resuspended and exposed to non-disulfide bond reducing or non-copper competing chaotropic conditions. Homogenizers, such as the Omnimixer™, can easily resuspend the insoluble fraction, even if it is a solid pellet. Sonicating the fraction can also break the insoluble fraction into particles small enough to resuspend.

In addition to the non-disulfide bond reducing or non-copper competing agent(s), other components may be needed to optimize the purification. Typically, a buffer will be added to maintain the pH of the solution. The actual desired pH range is not fixed; however, the insoluble desired product must remain insoluble. The pH may be adjusted within the desired range to aid in solubilizing contaminants. Salts, like NaCl, may also be advantageous, to better pellet the debris and possibly solubilize contaminants.

After the insoluble cell lysate fraction is exposed to non-disulfide bond reducing or non-copper competing chaotropic conditions, the resulting insoluble fraction must be separated from the soluble fraction. The same separation methods described above can be used. The insoluble fraction is then resuspended in disulfide bond reducing or copper competing chaotropic conditions. Again, the insoluble fraction can be resuspended according to the above methods. The disulfide reducing conditions may also optionally include a buffer, and salt in addition to the necessary components.

When purification is completed, the desired protein is soluble, and the copper may still be present. The copper can be removed by techniques known in the art (e.g. dialysis, desalting chromatography, diafiltration, or ultrafiltration). The desired protein may also be renatured according to known procedures. See U.S. Pat. No. 4,462,940. The recovered proteins may be assayed for activity depending on the nature of the desired protein. For example, proteins expressed for use in immunoassays are assayed by quantifying their antigenicity using the appropriate antibodies.

C. Examples

The examples presented below are provided as a further guide to the practitioner of ordinary skill in the art, and are not to be construed as limiting the invention in any way.

Example 1

E. coli Expression of a Superoxide Dismutase/HCV Antigen Fusion

D1210(pCF1EF/C33c) is an *E. coli* strain transformed with an expression vector encoding a SOD/HCV antigen fusion protein. This *E. coli* strain is a lac-repressor overproducing strain that carries the $lacI^q$ and $lacy^+$ alleles. Its genotype is $F^-$, $lacI^+$, $lacO^+, lacZ^+$, $gal^-$, $pro^-$, $leu^-$, $thi^-$, $end^-$, $hsm24^-$, $hsr^-$, $recA^-$, $rpsL^-$. The vector contains an expression cassette with the tacI promoter, the Shine Dalgarno sequences, a gene encoding human Cu/Zn superoxide dismutase (SOD), a peptide linker Glu-Phe-Gly, amino acids 1192 to 1457 of the HCV1 isolate of Hepatitis C Virus, and a peptide tail Ala-Glu-Phe. The expression vector also contains the ampicillin resistance gene and some pBR322 sequences. This transformed *E. coli* strain is described in E.P.O. Pub. Nos. 388 232 as pCF1EF/C33c, ATCC No. 67953.

An overnight culture was grown in 200 ml of L-broth supplemented with 0.2 mg vitamin B1 and 0.1 mg ampicillin at 30° C. Ten ml of the overnight culture were transferred to a 4 L shake flask with 1000 ml L-broth containing 10 mg/L of vitamin B1 and 50 mg/L of ampicillin. Four of these 1 L cultures were started and grown at 37° C. At an $OD_{650}$ of 0.8, the cells were induced with 1 mM IPTG and at the same time $CuSO_4$ was added to final levels of either 0, 1, 2, or 3 mM $Cu^{++}$. The cells were harvested seven hours after induction. Four hundred mls of media were removed from each culture, and spun. The media was removed, and the cells were stored at −80° C. overnight. The next day, the cell pellets were washed in TE (20 mM Tris buffer, pH 8.0 and 1 mM EDTA). The cells were disrupted by enzymatic digestion and sonication to produce cell lysates. Specifically, each cell pellet was resuspended in 15 ml TE containing 1 mg/ml of lysozyme and incubated for one hour at 4° C. The cells pellets were then sonicated with a Branson Sonifier 450 for 1–1.5 minutes at 70% power. The cell lysates were spun for five minutes at 15,000 rpm in a JA-20 rotor by a Beckman J2-21 centrifuge. The soluble fraction was decanted from the pelleted insoluble fraction. The insoluble fractions were resuspended in 5 ml of a solution of non-copper competing, non-disulfide bond reducing chaotropic conditions (20 mM Tris, pH 8.0, 1 mM EDTA, 8M urea). The resuspended insoluble pellets were incubated in this solution for five minutes at room temperature. The soluble fraction was separated by centrifuging the solution. Again, the soluble fraction was decanted from the insoluble pellet. The resulting pellets were resuspended in 5 ml of a solution of disulfide bond reducing copper competing chaotropic conditions (20 mM Tris, pH 8.0, 1 mM EDTA, 8M urea, and 50 mM DTT).

Samples were analyzed by SDS gel electrophoresis. A degree of purification was demonstrated where many non-proteinaceous contaminants were removed.

Example 2

E. coli Expression of Macrophage Colony Stimulating Factor

DG116(pLCSF221A) is an *E. coli* strain transformed with an expression vector encoding macrophage colony stimulating factor (M-CSF). This strain is described in U.S. Pat. No. 4,929,700 and is deposited at the ATCC, accession no. 67390. The vector contains an expression cassette with the pL promoter and a gene encoding amino acids 4 to 221 of the long clone of native M-CSF with a mutation at position 59 from a tyrosine to an aspartate. The expression vector also contains the ampicillin resistance gene.

An overnight culture was grown in 125 ml of L-broth with 10 mg/L of vitamin B1 and 50 mg/L of ampicillin. The next day, two 600 ml cultures were grown from the overnights at 30° C. to an $OD_{650}$ of roughly 1.0. From these cultures, 100 ml were transferred into 500 ml of prewarmed (at 37° C.) media in 4L shake flasks. Five of these cultures were started and incubated at 37° C. Copper sulfate was added to a final concentration of 0, 2.5, 3.0, 3.5, or 4.0 mM $Cu^{++}$ when the cultures were inoculated. The cells were harvested eight hours after induction. Cells were spun for 10 minutes at 3,000 rpm to remove the media. The cell pellets were washed in TE (20 mM Tris buffer, pH 8.0 and 1 mM EDTA), and were disrupted by enzymatic digestion and sonication to produce cell lysates. Specifically, each cell pellet was resuspended in 15 ml TE containing 1 mg/ml of lysozyme and was incubated for one hour at 4° C. The cells pellets were then sonicated with a Branson Sonifier 450 1–1.5 minutes at 70% power. The cell lysates were centrifuged for ten minutes at 10,000 rpm in a JA-20 rotor by a Beckman J2-21 centrifuge. The soluble fraction was decanted from the pelleted insoluble fraction. The insoluble fractions washed in 5 ml TE and resuspended in 5 ml of the same. One ml of each of the 5 ml suspensions was microfuged for ten minutes, and the soluble fraction was removed. The resulting pellets were resuspended in one ml of non-copper competing, non-disulfide bond reducing chaotropic conditions (20 mM Tris, pH 8.0, I mM EDTA, 8M urea). The resuspended insoluble pellets were incubated in this solution for ten minutes at room temperature. The soluble fractions were separated by microfuging at the same conditions. The resulting pellets were resuspended in 1 ml of a solution of disulfide bond reducing, copper competing chaotropic conditions (20 mM Tris, pH 8.0, 1 mM EDTA, 8M urea, and 50 mM DTT) and incubated at room temperature for ten minutes. The soluble fraction was separated by microfuging the solution.

From the SDS PAGE analysis, a significant purification was shown when the host cells were grown in the presence of copper. Many of the contaminants were soluble in non-disulfide bond reducing, non-copper competing chaotropic conditions.

Example 3

Yeast Expression of an Superoxide Sismutase/Insulin Fusion

PO17(pYSI3) is a yeast strain transformed having an expression vector with a SOD/Insulin coding sequence. The strain is 2150-2-3, whose genotype is (Mat a, ade 1, leu 2-04, cir°). Specifically, the expression vector comprised: the ADH2/GAP hybrid promoter, SOD gene linked to the human proinsulin gene by DNA sequence encoding NSGPT-PPSPGSPKR; and the a-factor terminator. The expression vector also contains a leucine selectable marker and the 2μ sequences. PO17(pYSI3) is described in U.S. patent application Ser. No. 07/680,046, which is the parent application to this application.

An overnight culture was grown in leu- media with 4% glucose at 30° C. From the overnight culture, a 10.7 ml culture was incubated in YEP plus 1% ethanol and 2 mM CuSO$_4$ at 30° C. and harvested at OD$_{650}$ of 5.9. The media was removed, and the pellet was washed with 20 mM EDTA and 0.9% NaCl. The resulting cell pellet was disrupted by vortexing the pellet six times at one minute intervals with one packed cell volume (~150 μl) of glass beads and two packed cell volumes (~300 μl) of 20 mM Tris-Cl pH 8+1 mM PMSF+1 μg/ml pepstatin (disruption buffer). (All buffers contained 1 mM PMSF and 1 μg/ml pepstatin.) The cell lysate was transferred to another tube, and the beads were washed twice with one packed cell volume (~150 μl) of disruption buffer. The washes were pooled with the cell lysate. The cell lysate was split into three aliquots; each aliquot was centrifuged for ten minutes in a microfuge, and the soluble fraction was removed. The remaining insoluble fractions were resuspended in approximately 200 μl of one of the following buffers; a) 50 mM sodium acetate, pH 3.5; b) 20 mM Tris-Cl, pH 8; or c) 50 mM glycine-OH, pH 10.5. The resuspended fractions were centrifuged, and the soluble fraction was removed. Each of the insoluble fractions was resuspended in a solution of non-disulfide bond reducing or copper competing chaotropic conditions (~100 μl of 2M urea in the appropriate (pH 3.5, 8, or 10.5) buffer) and incubated for 30 minutes at room temperature on a tilt-shaker. Each aliquot was split further into two portions (10 OD each) and centrifuged. The soluble fractions were removed. Next, each of the two pellets (the insoluble fractions) from the same pH extraction was resuspended in a 8M urea in buffer of the appropriate pH with and without 20 mM DTT, a disulfide reducing, copper competing chaotropic agent. Samples were incubated for 30 minutes at room temperature on a tilt-shaker and centrifuged. The soluble fraction was removed from the centrifuged sample.

Samples were assayed by SDS gel electrophoresis. The gel demonstrated that the desired protein, SOD/PI, was more soluble in the DTT solution. In a separate experiment without copper, the protein was solubilized under non-disulfide bond reducing, non-copper competing conditions. Many of the proteins seen in the total cell lysate were separated from the desired protein.

Example 4

Yeast Expression of a HIV-1 Antigen

JSC308(pJS178) is a yeast strain transformed with an expression vector with sequences encoding a HIV-1 gp-120 antigen. The yeast strain 1SC308 was Mat A, ura3Δ, leu 2-04, DM15, cir° and is described in EPO 340 986. The vector contained an expression cassette with a ADH2/GAP hybrid promoter (U.S. Pat. Nos. 4,876,197 and 4,880,734), a DNA fragment encoding amino acids 26 to 510 from the env region of the HIV-SF2 isolate (Luciw et at. *Nature* 312:760–763 (1984)), and the PYK terminator. Also included on the vector were the ampicillin resistance gene, 2μ sequences, and the URA3 and LEU2 genes.

A culture of the transformed yeast strain was grown in leu media with 5% glucose at 30° C. The next day 0.5 ml of the overnight culture was transferred to 10 ml YEP media with 2% glucose and 0.5 mM CuSO$_4$. The culture was incubated for 52 hours at 30° C. in a 125 ml flask. The cells were harvested by centrifuging five ml of the culture at 3,000 rpm in a J6B rotor for ten minutes at 4° C. in a Beckman J2-21 centrifuge. The cell pellet was washed with ten ml of 10 mM EDTA and centrifuged again. The washed cells were stored at −80° C. overnight. The cell pellet was added to 0.5 ml of 20 mM Tris-Cl, pH 8.0 (lysis buffer) and 1 mM EDTA and 0.5 ml of 0.5 mm acid washed glass beads. The mixture was vortexed eight times for one minute intervals to produce a cell lysate. The total cell lysate was separated from the beads. Then, 0.5 ml of lysis buffer was added to the beads and vortexed briefly. The wash liquid was removed from the beads and pooled with the cell lysate. The pooled material was microfuged for ten minutes at 4° C. The supernatant (or soluble fraction) was removed, and saved for analysis. The pellet was washed twice by resuspending the pellet by mixing with plastic rod and vortexing in 1 ml lysis buffer, followed by centrifugation in a microfuge. The supernatant (soluble fraction) was removed. The resulting pellet was resuspended in 1 ml lysis buffer.

To test the solubility properties of env2-3, a 100 μl aliquot was centrifuged for 2 minutes in the microfuge at 4° C. The supernatant was discarded, and the pellet was resuspended in 200 μl lysis buffer supplemented with 1% SDS (non-disulfide bond reducing, non-copper competing chaotropic conditions). After 15 minutes at room temperature, the solution was microfuged at room temperature. Then, the supernatant (soluble fraction) was removed, and the pellet was resuspended in 20 μl of lysis buffer supplemented with 1% SDS and 50 mM DTT (disulfide bond reducing, copper competing chaotropic conditions. After incubating the solution at room temperature for 15 minutes, the solution was centrifuged for 10 minutes at room temperature.

The proteins solubilized by the different methods were analyzed by SDS gel electrophoresis. The results demonstrated a dramatic purification of the desired protein. Nearly all the contaminants were soluble in the non-disulfide bond reducing, non-copper competing chaotropic conditions and were removed by the process of the invention.

Example 5

Yeast Expression of a HCV Antigen

JSC308(pSOD/E1) is a yeast strain transformed with an expression vector with sequences encoding SOD linked to the HCV E1 protein antigen. The yeast strain JSC308 was Mat A, ura3Δ, leu 2-04, DM15, cir° and is described in EP 340 986. The vector contained an expression cassette with a ADH2/GAP hybrid promoter (U.S. Pat. Nos. 4,876,197 and 4,880,734), a DNA fragment encoding amino acids 199 to 329 from the putative E1 protein of the HCV1 isolate (EPO 388 232), and the α-factor terminator. Also included on the vector were the ampicillin resistance gene, 2μ sequences, and the LEU2 gene.

A culture of the transformed yeast strain was grown in leu media with 5% glucose at 30° C. The next day 0.5 ml of the overnight culture was transferred to 10 ml YEP media with 2% glucose and 0.5 mM CuSO$_4$. The culture was incubated for 52 hours at 30° C. in a 125 ml flask. The cells were harvested by centrifuging five ml of the culture at 3,000 rpm in a J6B rotor for ten minutes at 4 ° C. in a Beckman J2-21 centrifuge. The cell pellet was washed with ten ml of 10 mM EDTA and centrifuged again. The washed cells were stored at −80° C. overnight. The cell pellet was added to 0.5 ml of 20 mM Tris-Cl, pH 8.0 (lysis buffer) and 1 mM EDTA and 0.5 ml of 0.5 mm acid washed glass beads. The mixture was vortexed eight times for one minute intervals to produce a cell lysate. The total cell lysates was separated from the beads. Then, 0.5 ml of lysis buffer was added to the beads and vortexed briefly. The wash liquid was removed from the beads and pooled with the cell lysate. The pooled material was microfuged for ten minutes at 4° C. The supernatant (or soluble fraction) was removed, and saved for analysis. The pellet was washed twice by resuspending the pellet by mixing with plastic rod and vortexing in 1 ml lysis buffer, followed by centrifugation in a microfuge. The supernatant (soluble fraction) was removed. The resulting pellet was resuspended in 0.5 ml of water.

To test the solubility properties of SOD/E1, a 100 µl aliquot was centrifuged for 5 minutes in the microfuge at 4° C. The supernatant was discarded, and the pellet was resuspended in 100 µl lysis buffer supplemented with 1% SDS (non-disulfide bond reducing, non-copper competing chaotropic conditions). After approximately one hour at room temperature, the solution was microfuged at room temperature. Then, the supernatant (soluble fraction) was removed, and the pellet was resuspended in 100 µl lysis buffer supplemented with 1% SDS and 50 mM DTT (disulfide bond reducing, copper competing chaotropic conditions. After approximately a 30 minutes incubation at room temperature, the solution was centrifuged for 10 minutes at room temperature.

The proteins solubilized by the different methods analyzed by SDS gel electrophoresis. The results demonstrated that a dramatic purification of the desired protein. Nearly all the contaminants were soluble in the non-disulfide bond reducing, non-copper competing chaotropic conditions. Also, increased expression was observed at 48 hours by Western analysis with an anti-SOD antibody.

What is claimed:

1. A method for producing a desired protein, which method comprises:
   (a) providing a host cell that expresses said desired protein;
   (b) culturing said host cell in a medium comprising an effective mount of $Cu^{++}$ wherein said desired protein is expressed as an insoluble aggregate;
   (c) disrupting said host cell to produce a cell lysate having a soluble fraction and an insoluble fraction;
   (d) removing contaminants from said insoluble fraction by incubating said insoluble fraction under non-disulfide-bond reducing chaotropic conditions; and
   (e) separating said soluble fraction from said insoluble fraction;
   (f) treating said insoluble fraction under disulfide-bond reducing chaotropic conditions to provide said desired protein.

2. The method of claim 1, wherein step (c) further comprises separating said soluble fraction from said insoluble fraction.

3. The method of claim 2, wherein said desired protein has at least one cysteine residue.

4. The method of claim 2, wherein said desired protein has at least two cysteine residues.

5. The method of claim 2, wherein said medium is highly aerated.

6. The method of claim 2, wherein said host cell is a yeast.

7. The method of claim 6, wherein said yeast is Saccharomyces.

8. The method of claim 6, wherein said $Cu^{++}$ is present in a concentration between 0.1 mM to 5 mM.

9. The method of claim 8, wherein said non-disulfide bond reducing chaotropic conditions comprise an effective amount of non-disulfide bond reducing chaotropic agent selected from the group consisting of sodium dodecyl sulfate and guanidine hydrochloride.

10. The method of claim 9, wherein said disulfide-bond reducing chaotropic conditions comprise an effective amount of dithiothreitol and sodium dodecyl sulfate.

11. The method of claim 1, wherein said desired protein is selected from the group consisting of SOD/E1, SOD/PI, SOD/PI/E1, env2-3, c25, and SOD/NS5.

12. The method of claim 2, wherein said host cell is *Escherichia coli*.

13. The method of claim 12, wherein said $Cu^{++}$ is present in a concentration between 1 mM to 10 mM.

14. The method of claim 12, wherein said non-disulfide-bond reducing chaotropic conditions comprise a non-disulfide bond reducing chaotropic agent selected from the group consisting of sodium dodecyl sulfate and guanidine hydrochloride.

15. The method of claim 14, wherein said disulfide-bond reducing chaotropic conditions comprise an effective amount of dithiothreitol and urea.

16. The method of claim 1, wherein said desired protein is selected from the group consisting of IL-2, IFN-β, M-CSF and c33c.

17. The method of claim 1, wherein said desired protein is heterologous to said host cell.

18. A method for producing a desired protein, which method comprises:
   (a) providing a host cell that expresses said desired protein;
   (b) culturing said host cell in a medium comprising an effective amount of $Cu^{++}$ wherein said desired protein is expressed as an insoluble aggregate;
   (c) disrupting said host cell to produce a cell lysate having a soluble fraction and an insoluble fraction;
   (d) removing contaminants from said insoluble fraction by incubating said insoluble fraction under non-copper competing chaotropic conditions; and
   (e) separating said soluble fraction from said insoluble fraction;
   (f) treating said insoluble fraction under copper competing chaotropic conditions to provide said desired protein.

19. The method of claim 18, wherein said desired protein is heterologous to said host cell.

* * * * *